US00PP19261P2

(12) United States Plant Patent
Korlipara

(10) Patent No.: US PP19,261 P2
(45) Date of Patent: Sep. 23, 2008

(54) *CAMPANULA* PLANT NAMED 'SUMMERTIME BLUES'

(50) Latin Name: ***C. punctata*×*C. trachelium***
Varietal Denomination: Summertime Blues

(75) Inventor: Harini Korlipara, Canby, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 0 days.

(21) Appl. No.: 11/904,691

(22) Filed: Sep. 27, 2007

(51) Int. Cl.
*A01H 5/00* (2006.01)

(52) U.S. Cl. ..... Plt./414

(58) Field of Classification Search ..... Plt./414, Plt./263
See application file for complete search history.

(56) References Cited

U.S. PATENT DOCUMENTS

PP13,194 P2 11/2002 Heims

*Primary Examiner*—Annette H Para
*Assistant Examiner*—S. B. McCormick-Ewoldt
(74) *Attorney, Agent, or Firm*—Klarquist Sparkman, LLP

(57) ABSTRACT

A new and distinct *Campanula* plant with large bells of deep violet colored flowers, multiple inflorescences, no seed set, and long bloom time (from May through September in Canby, Oreg).

1 Drawing Sheet

Botanical Classification: *Campanula* spp. (*C. punctata*× *C. trachelium*).
Variety Denomination: 'Summertime Blues'.

BACKGROUND OF THE INVENTION

The present invention relates to a new and distinct *Campanula* plant that is given the cultivar name of 'Summertine Blues'. *Campanula* is in the family *Campanulaceae. Campanula* 'Summertime Blues' originated from a planned cross between *Campanula punctata* 'Bowl of Cherries' (U.S. Plant Pat. No. 13,194), as the seed parent, and *Campanula trachelium* 'Bernice' (an unpatented plant), as the pollen parent. The offspring from the cross were planted out and this selection was made for its fine characteristics.

SUMMARY OF THE INVENTION

This new and unique *Campanula* hybrid is distinguished by:

1. Large bells of deep violet colored flowers;
2. Multiple inflorescences;
3. No seed set; and
4. Long bloom time (May through September in Canby, Oreg.).

This new cultivar has been reproduced only by asexual propagation (tissue culture). Each of the progeny exhibits identical characteristics to the original plant. Asexual propagation by division and tissue culture using standard micropropagation techniques with terminal and lateral shoots, as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

BRIEF DESCRIPTION OF THE PHOTOGRAPHS

FIG. 1 shows a close up of the flowers of a two-year-old *Campanula* 'Summertime Blues'.

FIG. 2 shows the new cultivar growing in the ground in the garden in full sun in July in Canby, Oreg.

DETAILED PLANT DESCRIPTION

The following is a detailed description of the new *Campanula punctata* based on observations of two year old specimen grown in the trail beds outside in full sun under typical weather in Canby, Oreg. Canby is Zone 8 on the USDA Hardiness map. Temperatures range from a high of 95 degrees F. in August to 32 degrees F. in January. Normal rainfall in Canby is 42.8 inches per year. The color descriptions are all based on The Royal Horticultural Society Colour Chart.

Plant:
- *Form.*—Rosette-forming herbaceous perennial.
- *Hardiness.*—USDA Zone 5–8.
- *Size.*—61 cm tall from the ground to the top of the inflorescence and 42 cm wide.
- *Habit.*—Upright, clumping, not many basal leaves.
- *Vigor.*—Excellent.

Leaf:
- *Type.*—Simple.
- *Arrangement.*—Basal and alternate up the stem.
- *Shape.*—Ovate to broadly ovate, except upper stem leaves which are lanceolate.
- *Venation.*—Main central vein with secondary veins palmate.
- *Margins.*—Incised and doubly serrate.
- *Apex.*—Acuminate.
- *Base.*—Cordate.
- *Blade size.*—Basal leaves from the ground are small, growing to 3 cm long and 2.7 cm wide; stem leaves are variable in size and shape, lower leaves are larger and petiolate, blades ovate growing to 6 cm long and 4 cm wide, pubescent on both sides, incised and doubly serrate, acuminate, truncate; leaves near the top and on side branches are smaller and sessile, blades lanceolate growing from 3 cm to 7.5 long and 1 cm to 3 cm wide, coarsely serrate, undulate, acuminate, cordate to truncate, pubescent on both sides.

*Surface texture.*—Pubescent on both sides.

*Petiole description.*—Basal leaves from the ground have petioles 5 cm long and 1 mm wide, pubescent, Greyed Purple 187A; lower stem leaves have petioles that grow to 11 cm long and 2 mm wide.

*Leaf color.*—Topside — closest to Yellow Green 147B with the main vein and margins tinted with Greyed Purple 187B; bottom side — same.

Inflorescence:

*Type.*—Panicle with 20 to 30 flowers.

*Peduncle.*—61 cm tall, pubescent, Yellow Green 146A tinted in sun with Greyed Purple 187A, internodes 4 cm to 9 cm, with 4 to 7 side branches.

*Pedicel.*—5 to 10 mm long and 1 mm wide, pubescent, Yellow Green 146A tinted in sun with Greyed Purple 187A.

*Bloom period.*—May through September in Canby, Oreg.

Flower bud:

*Size.*—1.5 cm wide and 4.8 cm long.

*Shape.*—Ovoid, elongate, pleated.

*Surface texture.*—Mostly glabrous, pubescent on main veins.

*Color.*—Between Violet Blue 92C and Violet Blue 90D.

Flower:

*Type.*—Actinomorphic.

*Shape.*—Campanulate.

*Size.*—5.5 cm long and 2.5 cm wide.

*Corolla.*—5 cm long; with tube 4 cm long and 5 lobes, 5 mm long and 5 mm wide, triangular, reflexed slightly, surface inside is pubescent and outside is glabrous except main veins which are pubescent, color outside is Violet Blue 90D, inside is Violet Blue 90A.

*Calyx.*—3 cm wide and 2.4 cm deep, campanulate with lobes flaring, tube 5 mm long and 15 mm wide at lobe junction, lobes are 15 mm long, 4 mm wide at the base, tips acuminate, pubescent on both sides, Yellow Green 146A tinted with Brown 200A.

*Stamen.*—5, filaments 3 mm long and 1 mm wide, White 155A, filaments are 12 mm long and less than 1 mm wide, Yellow 11B, sterile.

*Pistil.*—Ovary is 4 mm deep and 1 cm wide, Yellow White 158B, style 2.2 cm long and less than 2 mm wide, 3-branched stigma, each reflexed branch 5 mm long and 1 mm wide, Yellow Green 154D.

*Fragrance.*—Very slight.

*Lastingness.*—Each flower lasts for about 5 days on the plant.

Fruit and seed: None.

Diseases and pests: No diseases found of this new variety. No known diseases resistance. Many *Campanula* sp. are susceptible to snails, slugs, and aphids.

COMPARISON TO SIMILAR *CAMPANULA*

Compared to its seed parent, *Campanula punctata* 'Bowl of Cherries' (U.S. Plant Pat. No. 13,194), *Campanula* 'Summertime Blues' has deep violet rather than deep red purple colored flowers. The new variety is taller and is not rhizomatous.

Compared to its pollen parent, *Campanula trachelium* 'Bernice', an unpatented plant, the new variety has a single rather than a double flower. They have similar flower color. *Campanula trachelium* 'Bernice' is leafier than the new variety.

Compared to *Campanula* 'Mystic Bells', an unpatented plant, the near variety has deeper violet corolla color.

I claim:

1. A new and distinct *Campanula* plant as herein illustrated and described.

* * * * *

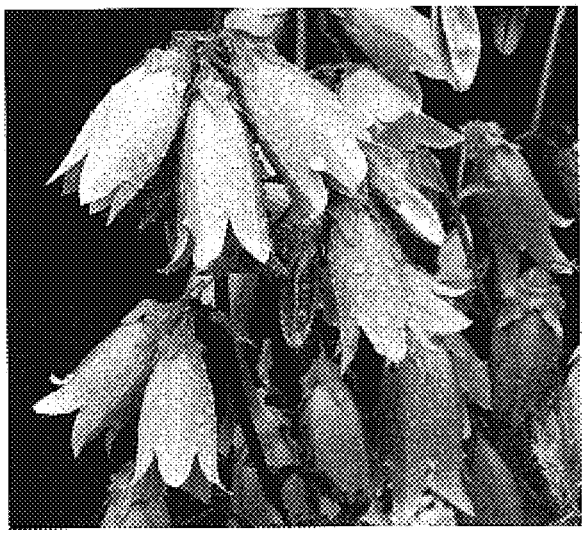
Figure 1 above, figure 2 below.
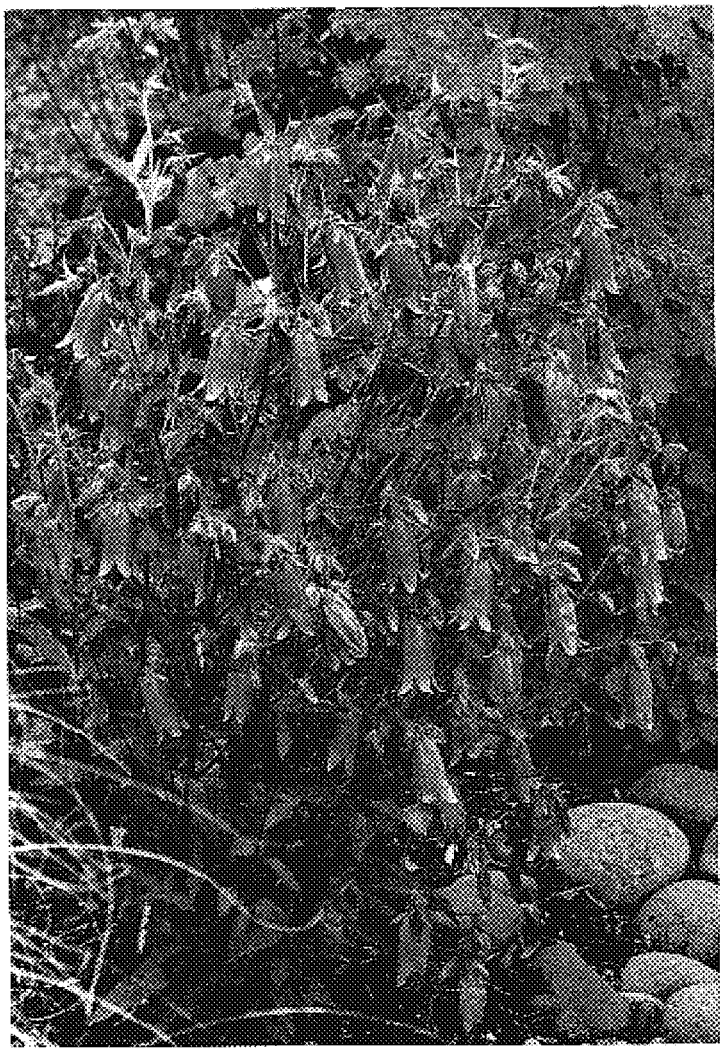

UNITED STATES PATENT AND TRADEMARK OFFICE

CERTIFICATE OF CORRECTION

PATENT NO. : PP 19,261 P2
APPLICATION NO. : 11/904691
DATED : September 23, 2008
INVENTOR(S) : Harini Korlipara It is certified that error appears in the above-identified patent and that said Letters Patent is hereby corrected as shown below:

In the Specification:

Column 1, line 8, “Summertine” should be --Summertime--.

Column 2, line 12, “trail beds” should be --trial beds--.

Column 4, line 20, “diseases” should be --disease--.

Column 4, line 36, “near” should be --new--.

Signed and Sealed this

Twenty-first Day of April, 2009

John Doll

JOHN DOLL
*Acting Director of the United States Patent and Trademark Office*